United States Patent
Bai et al.

(10) Patent No.: US 11,306,259 B2
(45) Date of Patent: Apr. 19, 2022

(54) METHOD AND APPARATUS FOR SELF-HEAT-EXTRACTING FLASH EVAPORATION OF SULFURIC ACID ALKYLATION REACTION PRODUCT

(71) Applicant: East China University of Science and Technology, Shanghai (CN)

(72) Inventors: Zhishan Bai, Shanghai (CN); Yan Zhang, Shanghai (CN); Xiaoyong Yang, Shanghai (CN); Huiqing Luo, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 283 days.

(21) Appl. No.: 16/665,233

(22) Filed: Oct. 28, 2019

(65) Prior Publication Data

US 2020/0165530 A1    May 28, 2020

(30) Foreign Application Priority Data

Nov. 28, 2018 (CN) .......................... 201811433727.3

(51) Int. Cl.
*C10G 29/28* (2006.01)
*B01D 3/06* (2006.01)
(Continued)

(52) U.S. Cl.
CPC .............. *C10G 29/28* (2013.01); *B01D 3/06* (2013.01); *C07C 2/62* (2013.01); *C07C 7/005* (2013.01);
(Continued)

(58) Field of Classification Search
CPC .................. C10G 29/28; C10G 57/005; C10G 2300/1081; B01D 3/06
See application file for complete search history.

(56) References Cited

U.S. PATENT DOCUMENTS

| 2,859,260 | A | * | 11/1958 | Stiles | ........................ C07C 2/54 |
| | | | | | 585/718 |
| 3,847,813 | A | * | 11/1974 | Castelli | .............. B01D 17/0211 |
| | | | | | 210/232 |
| 8,808,497 | B2 | * | 8/2014 | Duesel, Jr. | ............... B01D 1/14 |
| | | | | | 159/16.1 |

FOREIGN PATENT DOCUMENTS

| CN | 105964004 A | * | 9/2016 | ............... B01D 3/06 |
| CN | 105964004 A | | 9/2016 | |
| CN | 106190224 A | | 12/2016 | |

OTHER PUBLICATIONS

CN-105964004-A_English Translation (Year: 2016).*

* cited by examiner

*Primary Examiner* — Youngsul Jeong
(74) *Attorney, Agent, or Firm* — Marshall & Melhorn, LLC

(57) ABSTRACT

The present disclosure relates to a method and an apparatus for self-heat-extracting flash evaporation of a sulfuric acid alkylation reaction product. There is provided a method for self-heat-extracting flash evaporation of a sulfuric acid alkylation reaction product. One step is to coalesce and vaporize a preliminarily distributed sulfuric acid alkylation reaction product to cause preliminary vaporization of a hydrocarbon therein, thereby taking heat away and preliminarily separating the hydrocarbon from sulfuric acid. Another step is to subject the preliminarily separated alkylation reaction to reinforced separation, where the hydrocarbon is further vaporized to take heat away and further separate the hydrocarbon from the sulfuric acid. There is also provided an apparatus for self-heat-extracting flash evaporation of a sulfuric acid alkylation reaction product.

3 Claims, 1 Drawing Sheet

(51) Int. Cl.
  *C07C 2/62* (2006.01)
  *C07C 7/00* (2006.01)
  *C10G 57/00* (2006.01)
(52) U.S. Cl.
  CPC ... *C10G 57/005* (2013.01); *C10G 2300/1081* (2013.01)

METHOD AND APPARATUS FOR SELF-HEAT-EXTRACTING FLASH EVAPORATION OF SULFURIC ACID ALKYLATION REACTION PRODUCT

TECHNICAL FIELD

The present disclosure relates to an improved method and an improved apparatus for self-heat-extracting flash evaporation of a sulfuric acid alkylation reaction product, particularly to a method and an apparatus for self-heat-extracting flash evaporation wherein, after a reaction product effluent enters a flash tank, adjustment and distribution of a flow state, extraction of heat for vaporization, froth separation, separation and recovery of acid and hydrocarbons, and other processes are involved in sequence.

BACKGROUND ART

In recent years, with increasing concern on environmental protection, the sales volume of clean alkylated gasoline has increased rapidly year by year, and the development and production of alkylation processes have received increasing attention. At the same time, alkylated oil is a relatively stable, non-toxic compound with low volatility and a low sulfur content, and thus meets the increasingly stringent environmental requirements.

In the petroleum processing industry, alkylation means a process in which C2 to C5 low paraffins and olefins are subjected to addition reaction and polymerization reaction to form alkylated oils such as C8 isoparaffins under the catalysis of a strong acid such as sulfuric acid. Sulfuric acid alkylation is an exothermic process, wherein the heat is brought out by reaction effluents such as sulfuric acid, etc. At the same time, for the purpose of making full use of the reactants such as sulfuric acid and olefins, these reactants in the industry are often recycled to the reactor to participate in the alkylation reaction again. Hence, in order to enable the sulfuric acid alkylation reaction to occur at a lower temperature, heat has to be extracted from the sulfuric acid and hydrocarbons to decrease the temperature thereof before returning them to the reactor.

At present, vaporization of the hydrocarbons in the mixture is utilized to extract the heat from and thus cool the alkylation reaction product effluent in most cases. However, on one hand, due to the large difference in density between sulfuric acid and the mixed hydrocarbons, stratification can occur easily, resulting in insufficient mixing and contact, short contact time, and poor heat transfer effect in the transportation process. Consequently, the vaporization process of the mixed hydrocarbons often encounters the following problems in production: an insufficient vaporization rate, unsuccessful drop of the sulfuric acid temperature, clogging of the filler by impurities in the reaction product effluent, etc. On the other hand, when froth entrainment is serious in self-vaporization of the olefin and a large amount of sulfuric acid is entrained in the alkylation product, not only the utilization of sulfuric acid is lowered, but also the quality of the refined oil product is seriously degraded, and the setup is seriously corroded.

Chinese Patent ZL 201610519432.2 titled "METHOD FOR EXTRACTING HEAT FROM SULFURIC ACID ALKYLATION REACTION EFFLUENT BY FLASH EVAPORATION" describes a method for efficiently extracting heat from and cooling sulfuric acid and hydrocarbons by utilizing endothermic self-vaporization of the alkylation reaction product. This method is characterized by good effect of heat extraction and uniform temperature after heat extraction. Chinese Patent ZL2016105117417.4 titled "APPARATUS FOR SELF-HEAT-EXTRACTING FLASH EVAPORATION OF SULFURIC ACID ALKYLATION REACTION PRODUCT" describes a vertical flash tank, which includes, from the top to down, a liquid distributor, a bubble cap plate, an irregular microporous medium, a cyclone separator and an inclined plate separator. This apparatus has soundly solved the problems of a low hydrocarbon vaporization rate and an excessively high sulfuric acid temperature in the sulfuric acid alkylation production process. However, the above methods and apparatus have certain problems in practical use: when the reaction product effluent flows through the filler, the inclusions in the effluent are likely to clog the filler, so that the utilization of the filler is low, thereby leading to an insufficient vaporization rate of the hydrocarbons and thus insufficient heat extraction which renders the temperature of the sulfuric acid returning from the tank bottom unable to be lowered as desired; and the excessive amount of sulfuric acid entrained in the hydrocarbon phase renders the utilization of sulfuric acid not high.

Therefore, there is an urgent need in the art to develop a new method and apparatus for efficient heat extraction by means of flash evaporation.

SUMMARY

The present disclosure provides a novel method and a novel apparatus for self-heat-extracting flash evaporation of a sulfuric acid alkylation reaction product, thereby solving the problems existing in the prior art.

The technical problem to be solved by the present invention is to provide an effective method and an effective apparatus for efficient self-heat-extracting flash evaporation of an alkylation reaction product in allusion to the problems in the prior art, wherein a combined use of a coalescence-vaporization unit and a reinforced separation unit solves the following problems: in sulfuric acid alkylation production, the inclusions in the reaction product clog the filler, so that the utilization of the filler is low; heat extraction is insufficient during the self-vaporization of the mixed hydrocarbons, and the vaporization rate is low; froth entrainment during vaporization is serious; the preliminary recovery rate of the circulating acid is low, and the temperature is unduly high. The present invention greatly simplifies the alkylation refinery production process, while improving energy utilization and reducing production costs.

In one aspect, the present disclosure provides a method for self-heat-extracting flash evaporation of a sulfuric acid alkylation reaction product, comprising the following steps:

(a) coalescing and vaporizing a preliminarily distributed sulfuric acid alkylation reaction product to cause preliminary vaporization of a hydrocarbon therein, thereby taking heat away and preliminarily separating the hydrocarbon from sulfuric acid; and (b) subjecting the preliminarily separated alkylation reaction product obtained in step (a) to reinforced separation, wherein the hydrocarbon is further vaporized to take heat away and further separate the hydrocarbon from the sulfuric acid.

In a preferred embodiment, in step (a), the sulfuric acid alkylation reaction product is preliminarily distributed through a liquid distributor and a bubble cap plate; coalescence and vaporization are performed using a coalescence-vaporization unit, wherein the sulfuric acid alkylation reaction product flows into a center of a coalescence-vaporization assembly and, in its radial direction, flows sequentially through an inner wall of a support framework, a coalescence module, a vaporization module, and an outer wall of the support framework.

In another preferred embodiment, in step (b), the reinforced separation is performed using a reinforced separation unit, wherein acid droplets which are not separated timely are spread by an acid-hydrocarbon separation-coalescence baffle in the reinforced separation unit into a film on a surface thereof, adhered and detached, thereby further separating the hydrocarbon from the sulfuric acid; wherein the hydrocarbon is further vaporized, takes heat away, and is discharged from a gas phase outlet.

In another aspect, the present disclosure provides an apparatus for self-heat-extracting flash evaporation of a sulfuric acid alkylation reaction product, comprising:

a liquid distributor and a bubble cap plate disposed in a flash tank for preliminary distribution of a sulfuric acid alkylation reaction product;

a coalescence-vaporization unit disposed below the liquid distributor and the bubble cap plate in the flash tank for coalescing and vaporizing the sulfuric acid alkylation reaction product after the preliminary distribution, so that a hydrocarbon therein is preliminarily vaporized to take heat away and preliminarily separate the hydrocarbon from sulfuric acid; and a reinforced separation unit disposed below the coalescence-vaporization unit in the flash tank for reinforced separation of the preliminarily separated alkylation reaction product, wherein the hydrocarbon is further vaporized and takes heat away, thereby further separating the hydrocarbon from the sulfuric acid.

In a preferred embodiment, the coalescence-vaporization unit is consisting of one or more coalescence-vaporization assemblies arranged in parallel; and the coalescence-vaporization assembly comprises a support framework, a coalescence module and a vaporization module, wherein the support framework is a mesh structure consisting of a plurality of concentric cylinders; the coalescence module and the vaporization module are installed in an annular gap between the concentric cylinders; small holes having a diameter of 0-50 mm are opened through and around walls of the cylinders; and a ratio of a perforated area to an unperforated area of the wall is (1 to 1.5): 1.

In another preferred embodiment, a height of the coalescence-vaporization assembly is ⅙ to ¼ of a height of the flash tank; the coalescence module and the vaporization module are made of polymer fibers or modified metal fibers, wherein the coalescence module has a fiber diameter of 70-350 μm, and the vaporization module has a fiber diameter of 350-600 μm; wherein the fibers are alternately arranged in an irregular manner and are filled in the modules in a multi-stage porosity mode, wherein the multi-stage porosity mode is characterized by a total porosity of 50 to 95%, a first stage porosity of 50 to 70%, a stage-by-stage increment in porosity of 5% to 15% from inside to outside, a porosity of the coalescence module of less than 70-85%, a porosity of the vaporization module of not less than 85%, and an identical volume occupied by each module.

In another preferred embodiment, the reinforced separation unit is consisting of one or more acid-hydrocarbon separation-coalescence baffles and support members, and is disposed below the coalescence-vaporization unit, wherein the separation-coalescence baffle comprises a circular arc plate, a circular arc corrugated plate, a circular arc stepped plate or a bellmouth-shaped tubular structure formed by the above-mentioned circular arc plate structure and a cylindrical welded member; holes opened through the plate have a diameter of 0 to 50 mm; and a ratio of a perforated area to an unperforated area of the plate is (1 to 2): 1.

In another preferred embodiment, the separation-coalescence baffle is made of metal or non-metal; wherein an acidophilic fiber strand winds around a surface thereof, or tongue pieces are welded on the surface, with a winding or welding pitch on the surface of 5 to 100 mm, wherein the holes in the plate are bypassed during installation of the fiber strand or tongue pieces.

In another preferred embodiment, the acidophilic fiber strand is woven from one or more acidophilic fibers, wherein the fiber has a diameter of 100 to 500 μm, and the fiber strand has a diameter of 10 to 500 mm, wherein the acidophilic fiber strand winds in an inner surface of the circular arc plate in a circumferential direction; the tongue piece has a square, triangular, semi-elliptical, trapezoidal or semi-circular shape; the tongue piece has a height of 10 to 30 mm, which is the largest distance of the tongue piece from the baffle; the tongue piece has a thickness of 1 to 3 mm; the tongue piece is installed at an angle in the range of 15° and 75° in relation to the baffle; and a surface of the tongue piece may be treated with an acidophilic coating.

In another preferred embodiment, the flash tank has a reaction product inlet, a hydrocarbon phase outlet, and an acid phase outlet.

Beneficial Effects

The main advantages of the method and apparatus of the invention include:

A combination of a coalescence-vaporization unit and a reinforced separation unit reinforces the individual effect of each part, so that the coalescence degree of the acid and the vaporization degree of the hydrocarbon are enhanced. Hence, the heat released by the alkylation reaction can be utilized to the maximum extent, so that the reaction product maintains a high self-vaporization rate, while the temperature of the heat carrier such as sulfuric acid is lowered. At the same time, the vaporized hydrocarbon and the alkylation product are well separated. The influence of the liquid froth in the gas on the downstream compressor is reduced. Furthermore, the recovery rate of sulfuric acid is increased, and the consumption of sulfuric acid is reduced. Clogging of the coalescence-vaporization assembly by the inclusions in the reaction product is better avoided, and thus the utilization of the coalescence-vaporization assembly is increased effectively. At the same time, the production cost is reduced, and the economic efficiency is enhanced.

DESCRIPTION OF THE DRAWINGS

The accompanying drawings are provided for further understanding of the disclosure. They constitute a part of the specification only for further explanation of the disclosure without limiting the disclosure.

DETAILED DESCRIPTION

Figure 1:
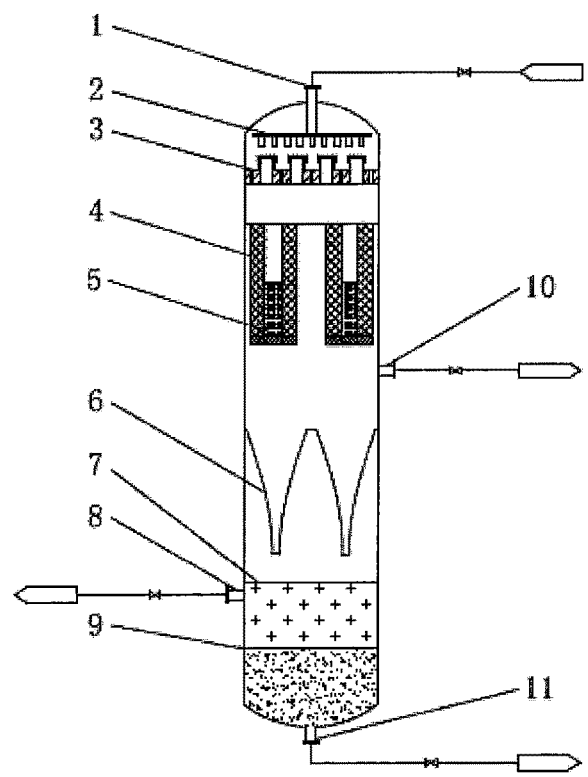
FIG. 1 shows a schematic view of an apparatus for self-heat-extracting flash evaporation of a sulfuric acid alkylation reaction product in accordance with an embodiment of the present invention.

After extensive and intensive research, the inventors of the present application have improved the framework for supporting the filler and the method for filling the filler on the basis of the existing method and apparatus for self-heat-extracting flash evaporation of a sulfuric acid alkylation reaction product. A coalescence-vaporization unit is used to achieve preliminary coarse separation of a mixture, and a reinforced separation unit is added to achieve deep acid-hydrocarbon separation. A well-organized combination of the coalescence-vaporization unit and the reinforced separation unit reinforces the acting process of each unit in use, and an ideal integrated technical effect is realized. The coalescence-separation performance of the apparatus is improved effectively, such that a significant decrease of the sulfuric acid temperature is better realized by heat extraction due to self-vaporization of the hydrocarbon in the sulfuric acid alkylation reaction product, and highly efficient separation of the hydrocarbon from the sulfuric acid is achieved. Consequently, the recovery rate of the sulfuric acid is also greatly increased. At the same time, the new framework for supporting the filler alleviates clogging of the filler by inclusions in the reaction product, such that the utilization of the filler is increased, thereby achieving better economic benefits.

In one aspect of the present disclosure, there is provided a method for self-heat-extracting flash evaporation of a sulfuric acid alkylation reaction product, comprising the following steps:

(a) after preliminary distribution by a liquid distributor and a bubble cap plate, first flowing a sulfuric acid alkylation reaction product into a coalescence-vaporization unit, wherein an acid-hydrocarbon mixture flows in a radial direction of a coalescence-vaporization assembly through an inner wall of a support framework, a coalescence module, a vaporization module and an outer wall of the support framework sequentially, such that the hydrocarbon is preliminarily coalesced and vaporized, and heat in the acid-hydrocarbon mixture is taken away due to heat absorption in the vaporization, thereby preliminarily separating the hydrocarbon from sulfuric acid; and (b) allowing the preliminarily separated alkylation reaction product to fall into a reinforced separation unit below, wherein acid droplets which are not separated timely are spread by an acid-hydrocarbon separation-coalescence baffle into a film on a surface thereof, adhered and detached; wherein the hydrocarbon is further vaporized with heat taken away, and is discharged from a gas phase outlet, thereby further separating the hydrocarbon from the sulfuric acid.

In the present disclosure, after coarse separation of the sulfuric acid alkylation reaction product in the coalescence-vaporization unit, the mixture is preliminarily separated and cooled; and then further subjected to deep separation in a reinforced separation unit, and the sulfuric acid temperature is further lowered.

In the present disclosure, in step (a), the sulfuric acid alkylation reaction product flows into the center of the coalescence-vaporization assembly, and sequentially passes in the radial direction thereof through the inner wall of the support framework, the coalescence module, the vaporization module and the outer wall of the support framework, thereby increasing the acid-hydrocarbon contact time and area, and reducing clogging of the coalescence-vaporization assembly.

In the present disclosure, in step (b), the special structure of the acid-hydrocarbon separation-coalescence baffle further separates the acid and hydrocarbon that are not separated in the previous separation step, wherein small acid droplets adhere to the surface thereof and form large-diameter acid droplets, and the hydrocarbon is also further vaporized.

In another aspect of the present disclosure, there is provided an apparatus for self-heat-extracting flash evaporation of a sulfuric acid alkylation reaction product, comprising:

a flash tank having a reaction product inlet, a hydrocarbon phase outlet, and an acid phase outlet;

a liquid distributor and a bubble cap plate disposed in the flash tank for preliminary distribution of the reaction product to make flow of the mixture uniform and stable;

a coalescence-vaporization unit disposed below the liquid distributor and bubble cap plate in the flash tank for passing the acid-hydrocarbon mixture through the coalescence-vaporization assembly to coalesce and vaporize the hydrocarbon, and coalesce the acid droplets to achieve separation; and a reinforced separation unit disposed below the coalescence-vaporization unit in the flash tank for further deep separation of the unseparated acid-hydrocarbon mixture using a separation-coalescence baffle, and further lowering the sulfuric acid temperature.

In the present disclosure, the coalescence-vaporization unit is consisting of one or more coalescence-vaporization assemblies arranged in parallel; and wherein the coalescence-vaporization assembly comprises a support framework, a coalescence module and a vaporization module, wherein the support framework is a mesh structure consisting of a plurality of concentric cylinders; the coalescence module and the vaporization module are installed in an annular gap between the concentric cylinders; small holes having a diameter of 0-50 mm are opened through and around walls of the cylinders; and a ratio of a perforated area to an unperforated area of the wall is (1 to 1.5): 1.

In the present disclosure, the coalescence-vaporization assembly has a height that is ⅙ to ¼ of the height of the flash tank; the coalescence module and the vaporization module are made of polymer fibers or modified metal fibers, wherein the coalescence module has a fiber diameter of 70 to 350 μm, and the vaporization module has a fiber diameter of 350 to 600 μm; wherein the fibers are alternately arranged in an irregular manner and filled in the modules in a multi-stage porosity mode.

In the present disclosure, the multi-stage porosity mode is characterized by a total porosity of 50 to 95%, a first-stage porosity of 50 to 70%, a stage-by-stage increment in porosity of 5% to 15% from the inside to the outside, a porosity of the coalescence module of less than 70-85%, a porosity of the vaporization module of 85% or higher, and an identical volume occupied by each module.

In the present disclosure, the reinforced separation unit is consisting of one or more acid-hydrocarbon separation-coalescence baffles and support members, and is disposed below the coalescence-vaporization unit, wherein the separation-coalescence baffle comprises a circular arc plate, a circular arc corrugated plate, a circular arc stepped plate or a bellmouth-shaped tubular structure formed by the above-mentioned circular arc plate structure and a cylindrical welded member; holes opened through the plate have a diameter of 0 to 50 mm; and a ratio of a perforated area to an unperforated area of the plate is (1 to 2): 1.

In the present disclosure, the material of the separation-coalescence baffle consisting of the circular arc plate, the circular arc corrugated plate, the circular arc stepped plate or the above circular arc plate structure and the cylindrical welded member is metal or non-metal; and an acidophilic fiber brand may wind around the surface of the baffle or tongue pieces may be welded on the surface, with a winding or welding pitch on the plate of 5 to 100 mm, wherein the holes in the plate are bypassed during installation of the fiber strand or tongue pieces.

In the present, disclosure, the acidophilic fiber strand is woven from one or more acidophilic fibers, wherein the fiber has a diameter of 100 to 500 and the fiber strand has a diameter of 10 to 500 mm, wherein the acidophilic fiber strand winds in an inner surface of the circular arc plate in a circumferential direction.

In the present disclosure, the tongue piece may have a square, triangular, semi-elliptical, trapezoidal, or semi-circular shape; the tongue piece has a height of 10-30 mm which is the largest distance of the tongue piece from the baffle; the tongue piece has a thickness of 1-3 mm; the tongue piece is installed at an angle in the range of 15° and 75° in relation to the baffle; and a surface of the tongue piece may be treated with an acidophilic coating.

Reference will be now made to the accompanying drawings.

FIG. 1 shows a schematic view of an apparatus for self-heat-extracting flash evaporation of a sulfuric acid alkylation reaction product in accordance with one embodiment of the present invention. As shown by FIG. 1, in operation, an alkylation reaction product that absorbs a large amount of heat of reaction enters a flash tank from a reaction product inlet 1 at the top of the flash tank. First, a liquid distributor 2 at the top of the tank is used to disperse the reaction product into a more uniform preliminary distribution state. Below the liquid distributor is a bubble cap plate 3 having weep holes. The alkylation reaction product from the liquid distributor flows to the bubble cap plate. Below the bubble cap plate is a coalescence-vaporization unit 4 for preliminary coalescence and vaporization. The coalescence-vaporization unit 4 is consisting of a coalescence-vaporization assembly. The coalescence-vaporization assembly comprises a support framework, a coalescence module and a vaporization module, wherein the support framework is a mesh structure consisting of a plurality of concentric cylinders. The coalescence module and the vaporization module are made of polymer fibers or modified metal fibers, wherein the fibers are filled in a multi-stage porosity mode. Small holes having a diameter of 0-50 mm are opened through and around the wall of the cylinder. The reaction product fluid 5 flows from the upper bubble cap plate into the center of the coalescence-vaporization assembly, and sequentially flows through the inner wall of the support framework, the coalescence module, the vaporization module and the outer wall of the support framework in the radial direction. This concentric annular structure not only greatly increases the cross-sectional area of the flow path and the heat transfer area between the sulfuric acid and the mixed hydrocarbons, but also allows the liquid at the center of the cylinder to maintain a stable liquid level as the fluid flows continuously into the center of the cylinder, so that the contact time between the liquid and the coalescence-vaporization assembly is prolonged greatly, and thus the heat transfer efficiency is increased significantly. At the same time, the inclusions in the reaction product settle at the bottom of the coalescence-vaporization assembly at the center, so that the probability of clogging the coalescence-vaporization assembly during the flow of the reaction product is greatly reduced, and thus the utilization of the coalescence-vaporization assembly is increased. The multi-stage porosity filling mode has the following advantages: the coalescence module having a small porosity improves the coalescence performance of the acid and hydrocarbon, while the vaporization module having a large porosity provides a carrier for vaporization of the mixed hydrocarbons, wherein the vaporization area is increased, and the separation efficiency is also improved. In addition, the fiber filaments in the coalescence-vaporization assembly have good wettability. On one hand, they can directionally induce convergence of sulfuric acid on the inner surface of a channel to form a liquid film. As the flow is continuously renewed, the contact area and contact probability between the sulfuric acid and the vaporized hydrocarbons are increased greatly, thereby enhancing the heat transfer efficiency between them. At the same time, the irregular, tiny porous channel structure in the coalescence-vaporization assembly causes continuous decrease of the medium pressure. When the medium pressure is lower than the saturated vapor pressure of the hydrocarbon, the hydrocarbon will be vaporized, and a large amount of heat is absorbed, so that the heat carrier such as sulfuric acid is cooled down. On the other hand, the porous channel makes it easier for the sulfuric acid droplets to coalesce into a mass on the inner surface of the channel, so that the sulfuric acid is more likely to leave the support and settle to the bottom of the flash tank.

The unvaporized hydrocarbon phase and sulfuric acid are prone to sedimentation and stratification at the bottom of the flash tank. In order to further improve the separation efficiency of sulfuric acid and hydrocarbon and reduce the amount of the liquid entrained in the gas, a reinforced separation unit 6 is disposed below the coalescence-vaporization unit, wherein the reinforced separation unit is consisting of one or more acid-hydrocarbon separation-coalescence baffles and support members. The separation-coalescence baffle comprises a circular arc plate, a circular arc corrugated plate, a circular arc stepped plate or a bellmouth-shaped tubular structure consisting of the above circular arc plate structure and a cylindrical welded member. Small holes having a diameter of 0 to 50 mm are provided in the baffle. Acid droplets pass through a bellmouth-shaped circular arc plate, circular arc corrugated plate, circular arc stepped plate or separation-coalescence baffle consisting of the above circular arc plate structure and a cylindrical welded member for further coalescence. The acidophilic fiber strand on the baffle makes it easier for the acid droplets to spread into a film, and the tongue piece makes the acid droplets prone to coalescence, so that the amount of acid entrained in the gas phase hydrocarbon is reduced, which facilities vaporization of the hydrocarbon phase and partial removal of the heat. The acid droplets coalesce into a mass which slides along the surface of the baffle, drops through the small holes in the baffle and settles at the bottom of the tank. In comparison with direct settlement of acid droplets from the coalescence-vaporization unit to the bottom of the tank, the separation-coalescence baffle increases the self-cooling time of the acid droplets on one hand, and on the other hand, the vaporization time and vaporization area of the hydrocarbon are also greatly increased, thereby increasing the vaporization rate of the hydrocarbon. In addition, the amount of sulfuric acid entrained in the gas phase hydrocarbon is reduced, and the separation efficiency of the sulfuric acid and hydrocarbon is also improved. A gas-liquid interface 7 and a liquid phase interface 9 are formed in the lower part of the tank. The hydrocarbon is further vaporized, takes heat away, and is discharged from the gas phase outlet 10. The unvaporized hydrocarbon is discharged from the hydrocarbon phase outlet 8; and the acid is discharged from the acid phase outlet 11.

Figure 2:
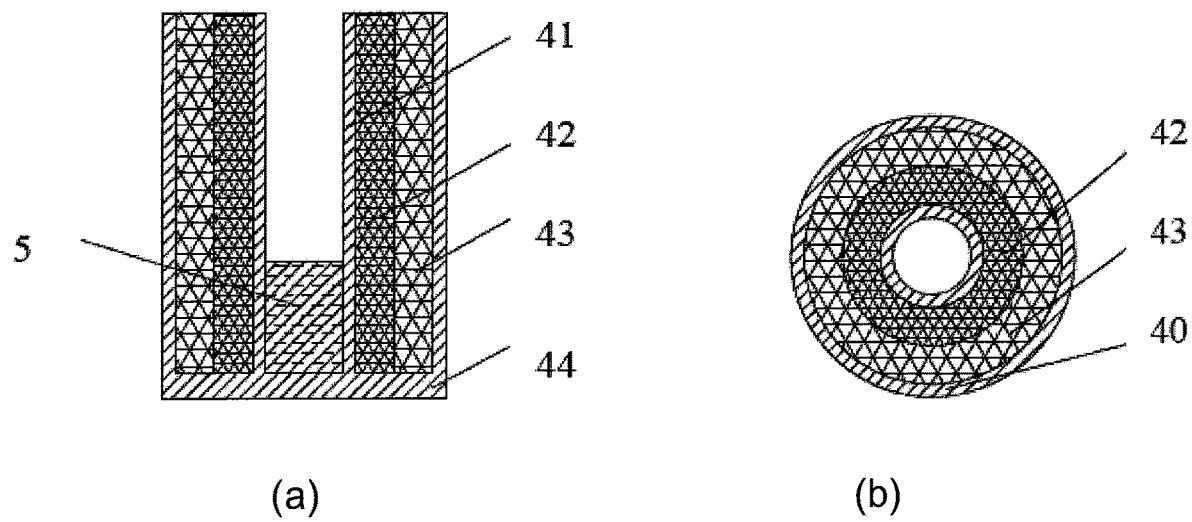
FIG. 2 is a schematic view of a coalescence-vaporization assembly according to an embodiment of the present invention, wherein (a) is a front view and (b) is a top view.

FIG. 2 is a schematic view of a coalescence-vaporization module according to an embodiment of the present invention, wherein (a) is a front view and (b) is a top view. As shown by FIG. 2(a), the reaction product fluid 5 flows from the upper bubble cap plate into the center of the coalescence-vaporization assembly, and sequentially flows through the inner wall 41 of the support framework, the coalescence module 42, the vaporization module 43 and the outer wall 44 of the support framework in the radial direction.

As shown by FIG. 2(b), the coalescence-vaporization assembly comprises a support framework 40, a coalescence module 42 and a vaporization module 43.

EXAMPLES

The invention will be further illustrated with reference to the following specific Examples. It is nevertheless to be appreciated that these Examples are only intended to exemplify the invention without limiting the scope of the invention. The test methods in the following examples for which no specific conditions are indicated will be carried out generally under conventional conditions or under those conditions suggested by the manufacturers. Unless otherwise specified, all parts are parts by weight, and all percentages are percentages by weight.

Example 1

The method and apparatus of the present invention were used in a domestic refinery for a pilot oil refining test of liquid phase alkylation using isobutane and butene as raw materials and sulfuric acid as a catalyst.

1. Experimental Conditions

In the pilot test, the reaction product effluent had a pressure of 0.08 MPa at the inlet of the flash tank, a flow rate of 850-1000 m$^3$/h, a temperature of 4-5° C., and an acid content of 40-50% (by volume).

2. Process Flow

As shown by FIG. 1.

3. Application Effects

Heat extraction was sufficient. Upon cooling, the temperature of the reaction product mixture at the bottom of the flash tank was −4.3° C., and the temperature difference between the vaporized hydrocarbon and the reaction product mixture at the bottom of the flash tank was only about 1° C. The mixed hydrocarbons had a high vaporization rate. The sulfuric acid had a stable return. The amount of the liquid entrained in the gas was significantly reduced, and the downstream compressor was running normally.

Example 2

The method and apparatus of the present invention were used in a domestic refinery for a pilot oil refining test of liquid phase alkylation using isobutane and butene as raw materials and sulfuric acid as a catalyst.

1. Experimental Conditions

In the pilot test, the reaction product effluent had a pressure of 0.09 MPa at the inlet of the flash tank, a flow rate of 900-1050 m$^3$/h, a temperature of 4-5° C., and an acid content of 45-55% (by volume).

2. Process Flow

As shown by FIG. 1.

3. Application Effects

Heat extraction was sufficient. Upon cooling, the temperature of the reaction product mixture at the bottom of the flash tank was −3.9° C., and the temperature difference between the vaporized hydrocarbon and the reaction product mixture at the bottom of the flash tank was only about 1° C. The mixed hydrocarbons had a high vaporization rate. The sulfuric acid had a stable return. The amount of the liquid entrained in the gas was significantly reduced, and the downstream compressor was running normally.

Example 3

The method and apparatus of the present invention were used in a domestic refinery for a pilot oil refining test of liquid phase alkylation using isobutane and butene as raw materials and sulfuric acid as a catalyst.

1. Experimental Conditions

In the pilot test, the reaction product effluent had a pressure of 0.08 MPa at the inlet of the flash tank, a flow rate of 600-700 m$^3$/h, a temperature of 3-4° C., and an acid content of 45-55% (by volume).

2. Process Flow

As shown by FIG. 1.

3. Application Effects

Heat extraction was sufficient. Upon cooling, the temperature of the reaction product mixture at the bottom of the flash tank was −4.8° C., and the temperature difference between the vaporized hydrocarbon and the reaction product mixture at the bottom of the flash tank was only about 1° C. The mixed hydrocarbons had a high vaporization rate. The sulfuric acid had a stable return. The amount of the liquid entrained in the gas was significantly reduced, and the downstream compressor was running normally.

The Examples listed above are only preferred examples in the disclosure, and they are not intended to limit the scope of the disclosure. Equivalent variations and modifications according to the disclosure in the scope of the present application for invention all fall in the technical scope of the disclosure.

All of the documents mentioned in the disclosure are incorporated herein by reference, as if each of them was incorporated herein individually by reference. It is to be further understood that various changes or modifications to the disclosure can be made by those skilled in the art after reading the above teachings, of the disclosure, and these equivalent variations fall in the scope defined by the accompanying claims of the application as well.

What is claimed is:

1. A method for self-heat-extracting flash evaporation of a sulfuric acid alkylation reaction product, comprising the following steps:
  (a) introducing a sulfuric acid alkylation reaction product to a coalescence-vaporization unit;
  (b) distributing the sulfuric acid alkylation reaction product throughout the coalescence-vaporization unit thereby producing a preliminarily distributed sulfuric acid alkylation product;
  (c) coalescing and vaporizing the preliminarily distributed sulfuric acid alkylation reaction product to cause preliminary vaporization of a hydrocarbon therein, thereby taking heat away and separating a preliminarily separated alkylation reaction product comprising hydrocarbon from the sulfuric acid,
  wherein said preliminarily distributed sulfuric acid alkylation reaction product is coalesced through one or more parallel coalescence-vaporization assemblies comprising a coalescence module and a vaporization module installed in an annular gap of a support framework comprising a plurality of concentric cylinders, wherein said preliminarily distributed sulfuric acid alkylation reaction product flows through 1-50 mm holes through and around said concentric cylinders to reach said coalescence module and said vaporization module, wherein a ratio of a perforated area to an unperforated area in a wall portion of one of said concentric cylinders is from 1:1 to 1.5:1, and wherein when said preliminarily distributed sulfuric acid alkylation reaction product flows through said coalescence module, said coalescence module coalesces the preliminarily distributed sulfuric acid alkylation reaction product; and (d) subjecting the preliminarily separated alkylation reaction product obtained in step (c) to reinforced separation by flowing said preliminarily separated alkylation reaction product through a circular arc plate, a circular arc corrugated plate, a circular arc stepped plate, or a bellmouth-shaped tubular structure formed by the above-mentioned circular arc plate structure and a cylindrical welded member, wherein said preliminarily separated alkylation reaction product flows through holes opened through the circular arc plate, the circular arc corrugated plate, the circular arc stepped plate, or the bellmouth-shaped tubular structure having a diameter of 1 to 50 mm, said holes creating a ratio of a perforated area to an unperforated area of the circular arc plate, the circular arc corrugated plate, the circular arc stepped plate, or the bellmouth-shaped tubular structure from 1:1 to 2:1, and wherein the hydrocarbon is further vaporized to take heat away from the preliminary separated alkylation reaction product and further separate the hydrocarbon from the sulfuric acid in the preliminarily separated alkylation reaction product.

2. The method of claim 1, wherein, in step (c), the preliminarily distributed sulfuric acid alkylation reaction product is preliminarily distributed through a liquid distributor and a bubble cap plate; and the coalescence and the vaporization are performed using a coalescence-vaporization unit comprising the one or more parallel coalescence-vaporization assemblies, wherein the preliminarily distributed sulfuric acid alkylation reaction product flows into a center of the coalescence-vaporization assemblies and, in its radial direction, flows sequentially through an inner wall of said support framework, said coalescence module, said vaporization module, and an outer wall of the support framework.

3. The method of claim 2, wherein, in step (d), the reinforced separation is conducted using a reinforced separation unit, wherein sulfuric acid droplets which are not separated timely are spread by an acid-hydrocarbon separation-coalescence baffle in the reinforced separation unit into a film on a surface thereof, adhered and detached, thereby further separating the hydrocarbon from the sulfuric acid; while the hydrocarbon is further vaporized, takes heat away, and is discharged from a gas phase outlet.

* * * * *